(12) United States Patent
Rastegar et al.

(10) Patent No.: US 10,190,937 B2
(45) Date of Patent: Jan. 29, 2019

(54) HIGH-G SHOCK TESTING MACHINE

(71) Applicant: Omnitek Partners LLC, Ronkonkoma, NY (US)

(72) Inventors: Jahangir S Rastegar, Stony Brook, NY (US); Jacques Fischer, Sound Beach, NY (US); Dake Feng, Kings Park, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 0 days.

(21) Appl. No.: 15/058,057

(22) Filed: Mar. 1, 2016

(65) Prior Publication Data

US 2016/0258837 A1 Sep. 8, 2016

Related U.S. Application Data

(60) Provisional application No. 62/129,791, filed on Mar. 7, 2015.

(51) Int. Cl.
*G01M 7/08* (2006.01)
*G01N 3/307* (2006.01)
*G01N 3/31* (2006.01)

(52) U.S. Cl.
CPC .............. *G01M 7/08* (2013.01); *G01N 3/307* (2013.01); *G01N 3/31* (2013.01)

(58) Field of Classification Search
CPC ............ G01M 7/08; G01N 3/307; G01N 3/31
See application file for complete search history.

(56) References Cited

U.S. PATENT DOCUMENTS

| | | | | |
|---|---|---|---|---|
| 3,430,481 | A * | 3/1969 | Shinbaum | G01M 7/08 73/12.04 |
| 3,757,562 | A * | 9/1973 | Goldberg | G01M 7/08 73/12.04 |
| 5,872,321 | A * | 2/1999 | Yannaccone | G01M 7/08 73/12.04 |
| 5,929,348 | A * | 7/1999 | Stein | G01M 7/08 73/12.07 |
| 6,213,564 | B1 * | 4/2001 | Face, Jr. | B60T 7/042 188/158 |
| 6,609,409 | B1 * | 8/2003 | Bock | G01M 7/08 73/12.01 |
| 6,675,631 | B1 * | 1/2004 | Steffan | G01M 17/0078 73/12.04 |
| 2014/0283579 | A1* | 9/2014 | Covic | G01M 17/0078 73/12.01 |
| 2015/0226635 | A1* | 8/2015 | Knott | G01M 7/08 73/12.04 |
| 2016/0161362 | A1* | 6/2016 | Rastegar | G01M 7/08 73/12.07 |

* cited by examiner

*Primary Examiner* — Natalie Huls

(57) ABSTRACT

A shock testing machine including: a test platform upon which one or more objects to be tested are mounted; one or more rails upon which the test platform is movable in a longitudinal direction; and a braking station for retarding a relative motion between the test platform and the braking station, wherein the test platform and the braking station include at least one portion interfering with the relative motion of the test platform and the braking station such that relative movement of the test platform and the braking station past the at least one portion produces a shock lateral to the longitudinal direction.

4 Claims, 8 Drawing Sheets

HIGH-G SHOCK TESTING MACHINE

CROSS REFERENCE TO RELATED APPLICATIONS

This application claims benefit to U.S. Provisional Application No. 62/129,791 filed on Mar. 7, 2015, the contents of which is incorporated herein by reference.

BACKGROUND

1. Field

The present invention relates generally to high-G shock testing machines, and more particularly to low-cost, reusable, "pseudo-static" testing machines and methods capable of imposing high acceleration and deceleration (>±10,000 g), opposing loads to a large (10-100+ lbs.) payload that are sustained over long durations (>5 msec). Such machine would provide the means for testing ordnance and commercial products/components under multi-axial loading, which includes both bending and shear moments. This includes the most extreme example of such events, namely "tail slap", where large lateral accelerations are introduced due to the bending and rebound of the product/component in the lateral direction, e.g., in the case of ordnance, perpendicular to the axis of penetration.

2. Prior Art

Gun-fired munitions, mortars and rail-gun munitions are subjected to high-G (setback and set-forward) acceleration during launch and target impact. Similar but more complex combinations of axial as well as lateral and bending shock loadings are experienced by air dropped weapons as they impact the target, particularly when the weapon is rocket assisted to achieve high impact velocities and when the target structure is highly heterogeneous, such as reinforced concrete or soil with large rock content. As a result, all components of the system and the system itself must survive such shock loading events and be qualified to such severe environments.

Developing a controllable test method and predictive capability to apply this environment in testing is critical to the development of fuze, energetic, and other weapon technologies. However, the corresponding change in velocity typically requires ballistic or operational testing. Both testing methods are extremely costly, personnel intensive, and introduce both technical and safety risks.

The vast majority of aircraft and satellite components, whether military or commercial, must be tested under certain shock loading conditions. That is, aircraft components must be shock tested to ensure that their design will survive its intended environment. Consequently, different aircraft components may have widely varying shock testing requirements. Currently, there is no one shock testing apparatus that can shock test aircraft components to accommodate the varying shock testing requirements for aircraft components, if at all. Thus, the industry resorts to building specialized shock testing machines or using computer simulation for shock testing, methods which are expensive and/or inaccurate.

In addition to rigorous vibration profiles, many consumer electronic components must be shock tested to determine how they will perform under certain shock conditions. Electronic components are often shock tested to determine how they will survive under unintended conditions, such as repetitive dropping. Of such consumer electronic components, device casings and circuit boards are often shock tested to determine survivability due abuse while other electronic devices are designed for heavy duty usage, such as in the construction trade and must be shock tested to determine if they are fit for their particular harsh environment. The current shock testing methods for consumer electronic devices have the same shortcomings as those described above with regard to commercial aircraft. Current shock testing machines in the consumer electronics area are either very simple drop testing from heights or pneumatic shock machines, both of which are inaccurate and their repeatability is unreliable.

Automobile components (as well as light and heavy duty truck components) must also undergo rigorous shock testing under normal use as well as components which can fail during a crash. Some automobile components must undergo shock testing to determine how they will perform under normal conditions, such as some structural frame components while other components must undergo shock testing to determine their performance during a crash, such as electronic components, steering wheels, airbags and the like. Like other shock testing machinery currently available in the areas of commercial aircraft and consumer electronics, the shock testing of automobile components are inaccurate, their repeatability is unreliable and they can also be relatively expensive.

SUMMARY

It is therefore an object to develop a low-cost, reusable testing method and accompanying experimental and simulation capabilities that can reproduce acceleration/time profiles representative of weapon target penetration as well as shock loading experienced by aircraft and other commercial products. This includes the experienced acceleration amplitude for a duration, or equivalently the integrated velocity change, in opposing shock-countershock mode, and multiple directions (multi-axial) for a sizable test article.

It is also appreciated that practical test considerations impose additional requirements beyond the required multi-axial acceleration/duration performance. Most tests call for more sensor channels than are recordable in an onboard recording system. In these instances, a nearly-stationary (i.e., "pseudo-static") test article or systems in which the test article undergoes limited and highly controlled resulting displacements that would allow the use of the desired number of sensor channels through direct cable harnesses, onboard recording systems and/or ultra-high speed RF or optical wireless communications. Another benefit of such shock testing systems is that off-board instrumentation is able to collect more channels of data with higher precision and sampling rates. One example of a pseudo-static testing is reverse ballistics where a target is propelled into a stationary and fully instrumented "Unit Under Test" (UUT).

It is also appreciated that it is critical that the shock testing system be scalable so that they would enable testing of both small UUTs and larger test vehicles. In this regard, the shock testing system can test articles ranging from circuit boards for consumer electronics weighing several ounces to ordnances/components weighing several hundred pounds.

In this disclosure, the following two novel classes of shock/tail-slap testing machine concepts are presented:

1. A class of multi-axial shock loading machines for applying short duration high acceleration and deceleration pulses of over ±10,000 g over long periods of time of well over 5 msec. These shock loading machines can apply one or a combination of shock loading pulses to the UUT in the axial and lateral directions to simulate almost any shock loading events, including the "tail slap", where large lateral accelerations are introduced due to the bending and rebound of an ordinance in the lateral direction.

2. A class of high and long duration shock loading machines to simulate penetration shock loading with the capability of simultaneously applying relatively short and/or long duration lateral shock loadings to simulate "tail slap" events where lateral accelerations are introduced due to the bending and rebound of the ordnance in the lateral direction. In these machines, the penetration shock loading is generated by braking forces applied to the test platform over which the ordnance being tested is mounted. Lateral shock loading of the platform generates vibratory motion of the platform to generate the lateral shock loading events. The braking forces as well as shock loading levels may be varied to generate the desired shock loading profiles.

In addition, methods are presented for accurately modelling both the test conditions and the test article.

The development of such shock testing machines having relatively low-cost to construct and operate, being reusable, and that uses "pseudo-static" testing techniques or similar techniques that are capable of imposing high acceleration and deceleration (>±10,000 g), opposing loads to a large (10-100+ lbs.) payload that are sustained over long durations (>5 msec).

The two novel classes of shock/tail-slap testing machine concepts provide "Ordnance Shock/Tail-Slap Replicator" systems that provide the means for testing ordnance under multi-axial loading, which includes both bending and shear moments. This includes the most extreme example of such events, namely "tail slap", where large lateral accelerations are introduced due to the bending and rebound of the weapon in the lateral direction, i.e., perpendicular to the axis of penetration.

Accordingly, a shock testing machine is provided. The shock testing machine comprising: a test platform upon which one or more objects to be tested are mounted; one or more rails upon which the test platform is movable; and a braking station having one or more braking elements operatively engageable with one or more corresponding braking surfaces on the test platform after the test platform has moved a predetermined distance relative to the braking station, wherein the one or more braking elements are movable to vary a gap between the one or more braking elements and the one or more braking surface.

The shock testing machine can further comprise one or more actuators for moving the braking elements. The one or more actuators can comprise one or more piezoelectric actuators.

The one or more braking elements can comprise a beveled region such that a portion of the braking element in the beveled region has a thickness that increases with a direction of travel of the test platform.

A method for shock testing one or more objects is also provided. The method comprising: mounting the one or more objects to a test platform; movably disposing the test platform on one or more rails; moving the test platform a predetermined distance relative to a braking station; varying a braking amount of the braking station by varying a gap between one or more braking elements at the braking station and one or more corresponding braking surfaces at the test platform; and braking the test platform by contacting the one or more braking elements with the corresponding one or more braking surfaces.

Also provided is a shock testing machine comprising: a test platform upon which one or more objects to be tested are mounted; one or more rails upon which the test platform is movable in a longitudinal direction; and a braking station for retarding a relative motion between the test platform and the braking station, wherein the test platform and the braking station include at least one portion interfering with the relative motion of the test platform and the braking station such that relative movement of the test platform and the braking station past the at least one portion produces a shock lateral to the longitudinal direction.

The at least one portion comprises one or more protuberances on the test platform and one or more protuberances on the braking station, wherein the one or more protuberances on the test platform overlap with the one or more protuberances on the braking station in a direction lateral to the longitudinal direction. The shock testing machine can further comprise one or more actuators for varying an amount of the overlap in the direction lateral to the longitudinal direction. The one or more actuators can comprise one or more piezoelectric actuators.

The test platform can be rotatable about a pivot such that the one or more protuberances on the test platform is movable in the direction lateral to the longitudinal direction. The test platform can be biased to resist rotation about the pivot.

The braking station can be stationary relative to the test platform.

The braking station and test platform can be movable relative to each other. The shock testing machine can further comprise one or more second rails upon which the braking station is movable in the longitudinal direction.

Also provided is a method for shock testing one or more objects. The method comprising: mounting the one or more objects to a test platform; movably disposing the test platform on one or more rails; moving the test platform in a longitudinal direction a predetermined distance relative to a braking station; and causing an interference between the test platform and the braking station such that relative movement of the test platform and the braking station past the at least one portion produces a shock in a direction lateral to the longitudinal direction. The method can further comprise varying an amount of the interference in the direction lateral to the longitudinal direction.

Also provided is a shock testing machine comprising: a test platform for holding one or more objects to be shock tested, the test platform having an impact surface; a fixed member having a surface disposed a predetermined distance from a corresponding surface of the test platform, the test platform being movable such that the surface of the test platform can contact the corresponding surface of the fixed member upon an impact to the impact surface; and a flywheel having one or more cams for contacting the impact surface upon rotation of the flywheel such that the impact of each of the one or more cams on the impact surface causes the surface of the test platform to impact the corresponding surface of the fixed member to produce a shock in the one or more objects to be tested. The shock testing machine can further comprise a biasing member for biasing the surface of the test platform away from the corresponding surface of the fixed member.

The impact surface can comprises first and second impact surfaces, the fixed member can comprise first and second surfaces each disposed a predetermined distance from a corresponding first and second surface of the test platform, the test platform being movable such that the first and second surfaces of the test platform can contact the corresponding first and second surfaces of the fixed member upon an impact to the first and second impact surfaces, and the flywheel can comprise first and second flywheels each having one or more cams for contacting a corresponding first and second impact surface upon rotation of the first and second flywheels.

The one or more cams can comprise a plurality of cams equally spaced along a circumference of the flywheel.

The one or more cams can be biased radially outward from the flywheel.

BRIEF DESCRIPTION OF THE DRAWINGS

These and other features, aspects, and advantages of the apparatus of the present invention will become better understood with regard to the following description, appended claims, and accompanying drawings where:

DETAILED DESCRIPTION

While the present shock-loading devices and methods may have particular utility with regard to testing shock loading of articles for use in ordnances, such shock loading devices and methods also have utility in testing other articles for use in military and commercial aircraft as well as commercial products, such as automobile and consumer electronic components. Thus, without limiting the applicability of such shock-loading devices and methods to articles for use in ordnances, the present disclosure will discuss embodiments with regard to shock loading of articles for use in ordnances by way of example.

A first embodiment of shock and shock/tail-slap testing machines are variations based on the basic design of the shock testing machine described in U.S. application Ser. No. 14/500,921 filed on Sep. 29, 2014, the disclosure of which is incorporated herein by reference. The machines of the first embodiment provide high and relatively long duration axial shock loading, which could be made varying in time, while providing a number of tail-slap producing (lateral) shock loadings of different amplitudes and durations resulting in bending vibratory loading of the testing object.

A second embodiment of shock and shock/tail-slap testing machines are for applying short duration and high acceleration/deceleration pulses, such as of over ±10,000 g over durations of e.g., over 5 msec. These shock loading machine concepts can apply one or a combination of shock loading pulses to the article being tested, such as an ordnance, in axial and lateral directions to simulate almost any shock loading events, including tail slap, where large lateral accelerations/decelerations are introduced due to the bending and rebound in the lateral direction. For purposes of this disclosure, "tail-slap" means a shock loading event in a direction perpendicular to its intended motion, such intended motion being in a direction of penetration with regard to an ordinance. For other articles being testing, the term shock loading event is merely in a direction created by the machine with regard to an orientation of the article being tested in the machine.

The first embodiment of shock and shock/tail-slap testing machines are variations based on the basic design of the Omnitek shock testing machine described in U.S. application Ser. No. 14/500,921 filed on Sep. 29, 2014. The machines of the first embodiment can provide high and relatively long duration axial shock loading, which could be made time varying, while providing a number of tail-slap producing (lateral) shock loadings of different amplitudes and durations that result in bending vibratory loading of the article being tested. The design of the shock loading machine can achieve high-G shock loading, such as up to 3,000 G (and time varying if desired) with a durations of up to 3 msec.

Figure 1:
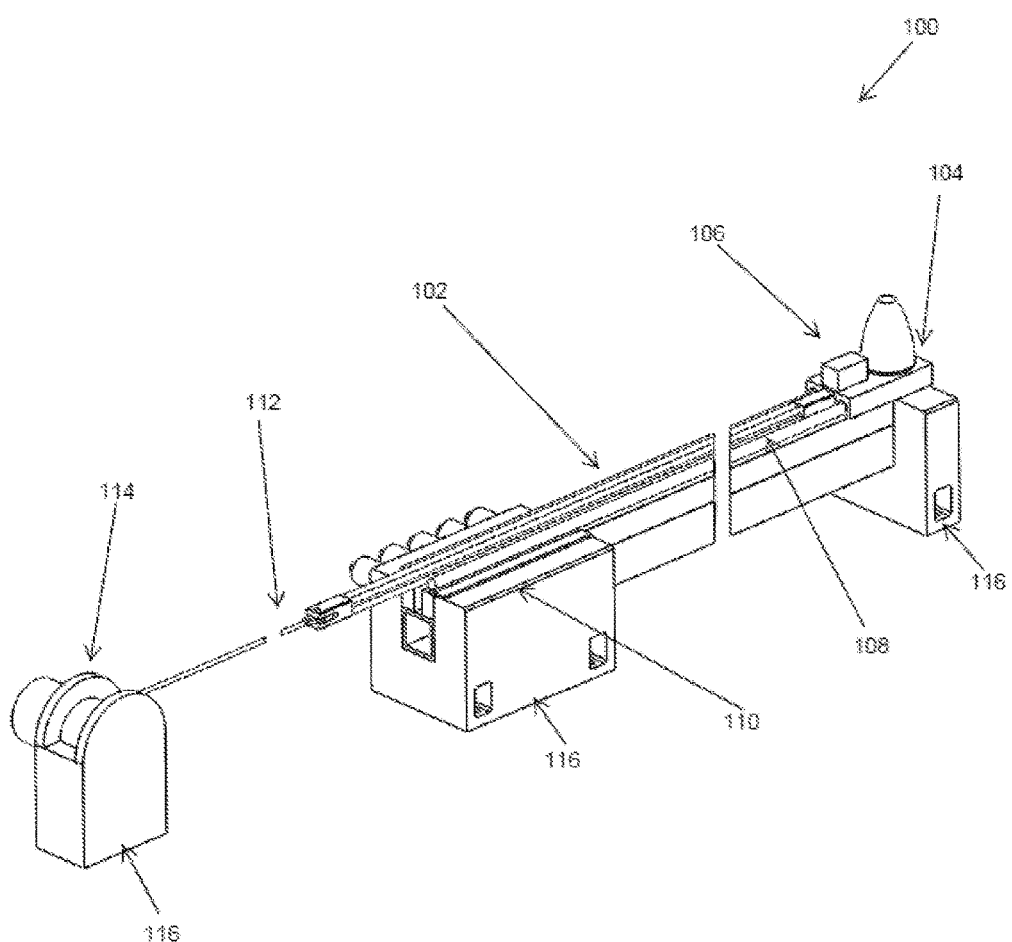
FIG. 1 illustrates a perspective view of a first embodiment of a shock testing machine.

The shock testing machine of the first embodiment is shown in FIG. 1, generally referred to by reference numeral 100. In FIG. 1, the breaks on the left and right of the machine are used to denote a long length of the components being broken. In this design, the machine 100 is laid down horizontally to allow the use of longer test platform travel and the use of longer length bungee cords 102 to provide large accelerating forces to the test platform 104 over the entire range of its travel. The test objects 106 are mounted over the test platform 104 using mounting means specific to the type of object and the testing required. The test platform 104 is accelerated on one or more guide rails 108 towards a braking station 110 having braking elements (described below) by locking the test platform 104 from movement, tensioning the bungee cords 102 with the bungee tensioning cable 112 and winch 114 and then releasing the test platform 102 to allow the tension in the bungee cord(s) 102 to accelerate the test platform 104 towards the braking station 110, similarly to that of the shock testing machine described in U.S. application Ser. No. 14/500,921 and its braking force is similarly adjusted, however, as will be described below, such braking force may be varied during the braking event. The above components may be integrated into another machine or provided with one or more bases 116 for stability.

Figure 2:
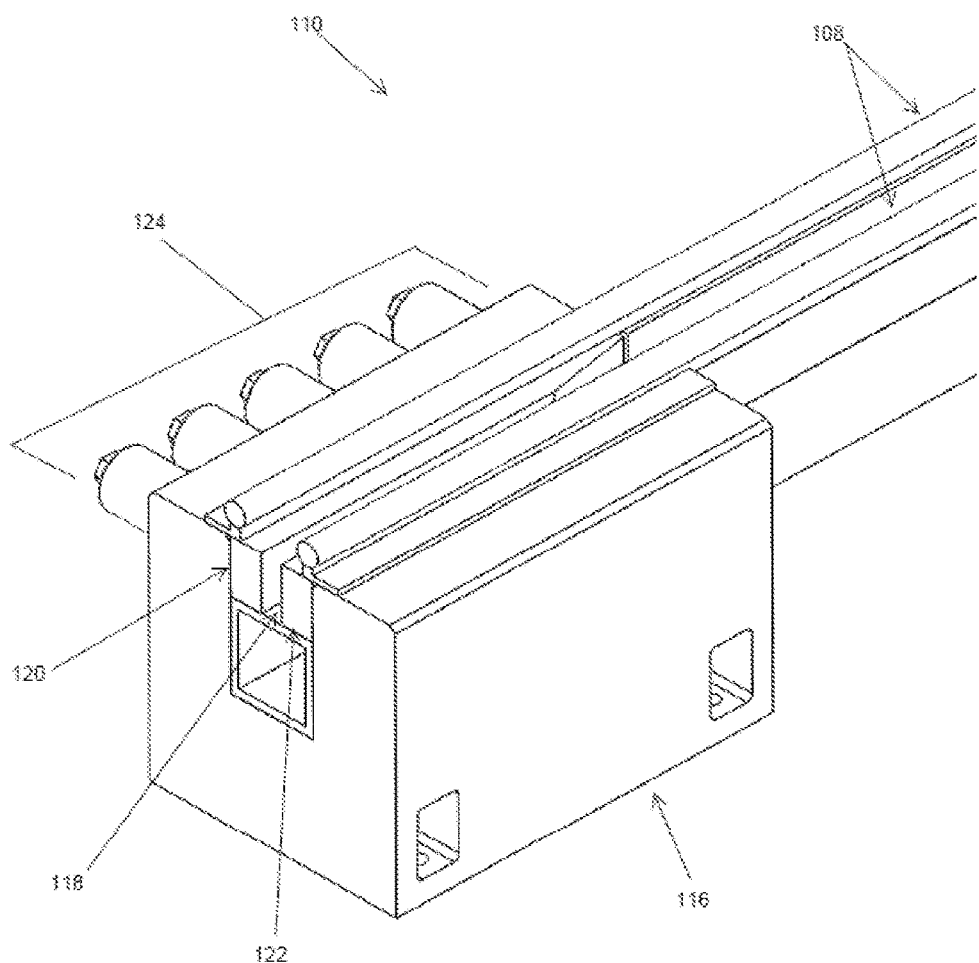
FIG. 2 illustrates a perspective view of the braking station of the shock testing machine of FIG. 1.

A close up view of the braking station 110 of the shock loading machine 100 of FIG. 1 is shown in FIG. 2. In the shock loading machine 100, the braking station 110 is provided with a "brake engagement pathway" 118 with an adjustable gap for braking force adjustment. The brake engagement pathway 118 is provided with a similar "brake force adjustment element" 120 on one side of the brake engagement pathway 118, which in FIG. 2 and for the sake of simplicity is shown to be made of a single rigid piece, but may be constructed with two or more segments that are joined to a single relatively thin, flexible in bending but hard spring steel facing braking pads 122 on the other side of the brake engagement pathway 118. The brake force adjustment element(s) 120 are movable into and out from the brake engagement pathway 118. Brake force adjustment actuators 124, such as large diameter piezoelectric axial actuation elements of around 5-7 cm long may then be used to selectively move the brake force adjustment element(s) to vary the braking forces applied to the corresponding braking surfaces, such as braking pads 126 (see FIG. 3), of the test platform 104, thereby allowing the deceleration rate of the test platform 104 and thereby the test object 106 to be time varied. It will be appreciated by those skilled in the art that by using relatively thin braking pads of the order of 4-5 mm, by varying the gap in the brake engagement pathway 118 a very small amount, such as just 3-4 microns, the braking force can be varied significantly. Therefore the use of axial piezoelectric actuators are capable of allowing the machine 100 to significantly vary the deceleration rate of the test object 106 as it is decelerated to a stop.

Figure 3:
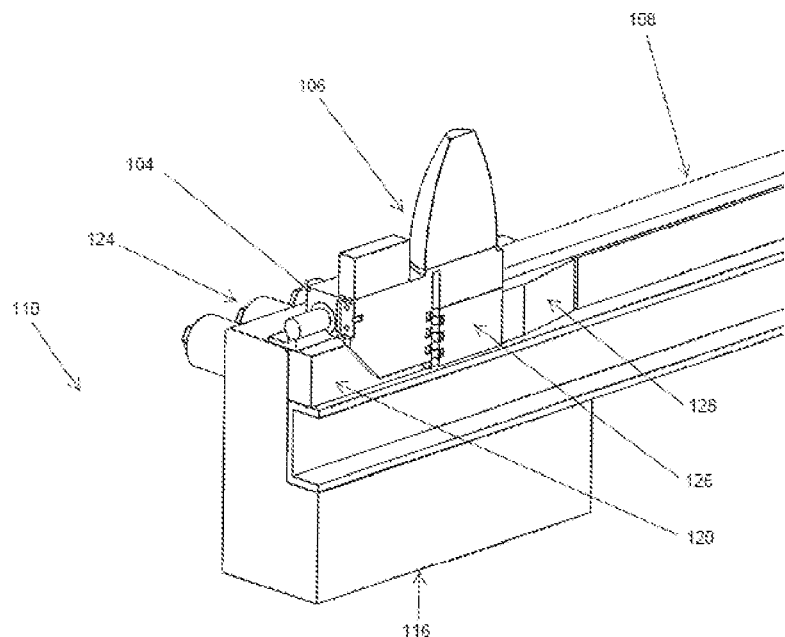
FIG. 3 illustrates a perspective cutaway view of the braking station of FIG. 2 showing engagement with the test platform.

A cutaway view of the braking station 110 showing engagement of the test platform brakes with the surfaces of the brake engagement pathway gap walls is shown in FIG. 3. Half of the braking station is not shown in FIG. 3 so that the braking pads 126 are visible. As can be seen, the brake engagement pathway walls are provided with an initial beveled region 128 to ensure smooth initial engagement with the braking pads 126 (only one side is shown in FIG. 3, another braking pad is on the other side of the test platform 104 not visible in FIG. 3). Although only one pair of braking pads 106 is employed in FIGS. 2 and 3, however, for higher braking force levels corresponding to heavier payloads as well as higher shock loading acceleration levels, multiple pairs of such braking pads 126 may be used to distribute the braking forces over larger braking pad surfaces.

Figure 4:
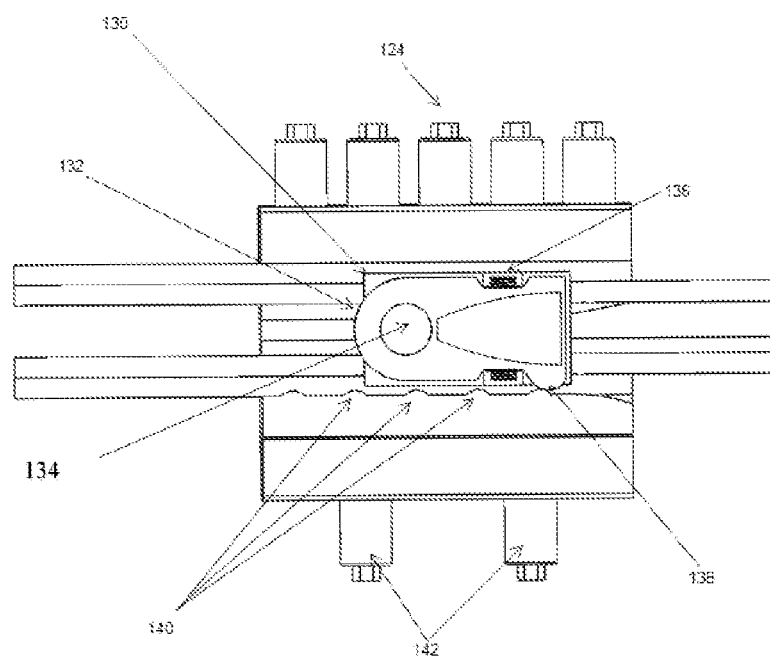
FIG. 4 illustrates a top view of a variation shock testing machine having an alternative test platform and moving carriage.

Referring now to FIG. 4, there is illustrated a variation of the first embodiment of shock testing machine, which the test platform of FIGS. 1-3 is replaced by a "moving carriage" 130 to which a test platform 132 is attached by a rotary joint 134, as shown in FIG. 4. In FIG. 4, features similar to those described with regard to FIGS. 1-3 use the same reference numerals as in FIGS. 1-3. As the moving carriage 130 is accelerated towards the braking station 110 by the pre-tensioned bungees 102, the test platform 132 is held in its nominal orientation relative to the moving carriage shown in FIG. 4 by the indicated "preloaded test platform to moving carriage springs" 136. Then, as the braking pads 126 mounted on the moving carriage 130 engage the walls of the brake engagement pathway 118 as described for the shock loading machine of FIGS. 1-3, a "tail-slap producing protuberance" 138 provided on the test platform 132 will engage "tail-slap producing humps" 140 which are fixed to the structure of the braking station 110, thereby imparting a short duration lateral impulse to the test platform 132, causing it to start to vibrate rotationally about the platform rotary hinge 134. The amplitude of the imparted impulse may be adjusted by the provided tail-slap adjustment actuators 142 that control lateral positioning of the humps. By providing stops to limit the rotary motion of the test platform 132 relative to the moving carriage 130, higher tail-slap producing lateral shock loading may also be produced.

Figure 5:
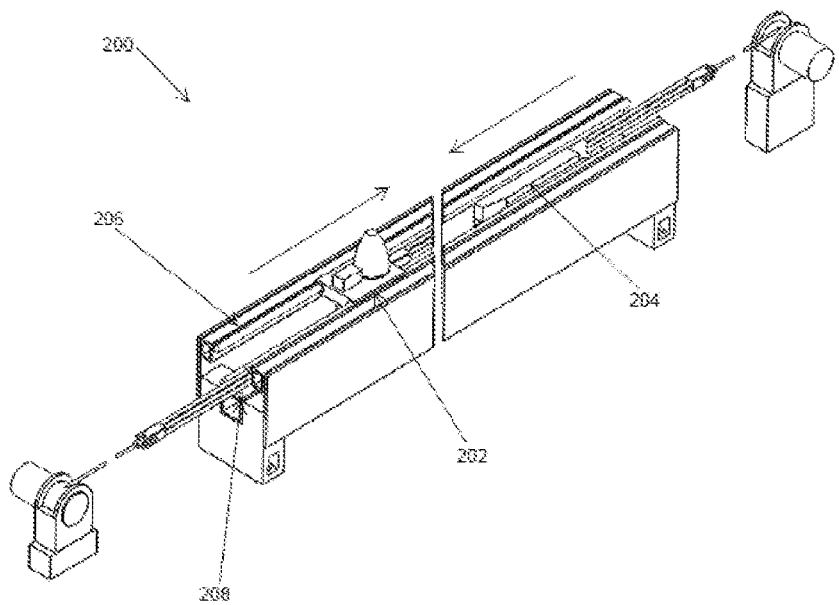
FIG. 5 illustrates a perspective view of another alternative shock testing machine in which the test platform and braking unit are accelerated towards each other.

For the axial and axial/tail slap testing machines of FIGS. 1-3 and 4, respectively, the maximum shock loading levels and durations are limited to the maximum achievable velocity of their testing platform, i.e., the velocity at which the braking pads engage the stationary walls of the brake engagement pathway gaps. Another variation of a shock testing machine is shown in FIG. 5, referred to generally by reference numeral 200. In FIG. 5, the breaks on the left, center and right of the machine are used to denote a long length of the components being broken. In the shock testing machine 200 of FIG. 5, the test platform 202 as well as the braking unit 204 are movable towards each other over separate pairs of overlaying rails 206 (corresponding to the test platform 202) and 208 (corresponding to the braking unit). All other components are similar to those discussed above. The test platform 202 and the braking unit 204 are accelerated towards each other as shown by the arrows, thereby allowing them to reach twice the relative velocity as the test platform could reach relative to a stationary braking unit. As a result, the axial shock/tail-slap testing machine can achieve significantly higher shock loading levels, or when desired, higher shock loading duration.

Figure 6:
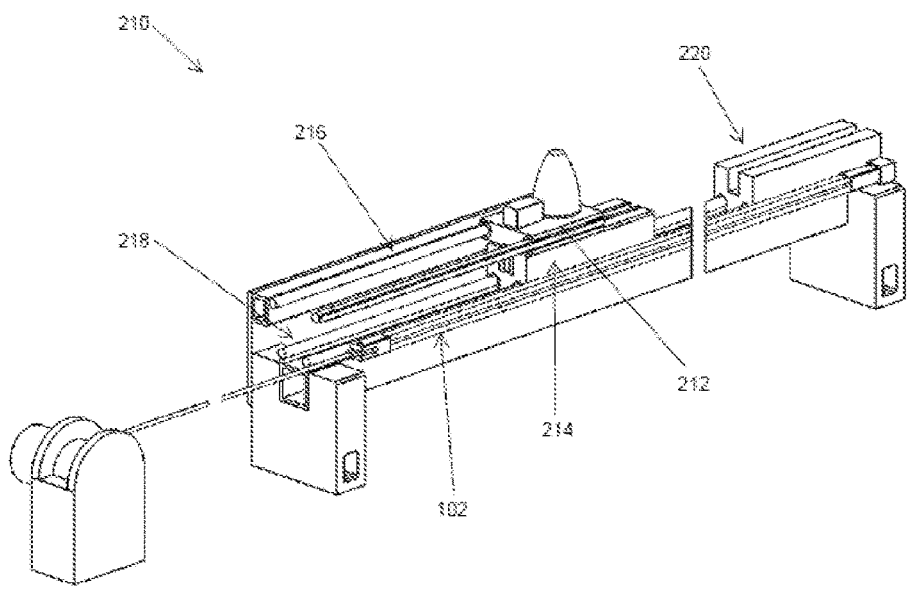
FIG. 6 illustrates a perspective view of another variation of shock testing machine of the first embodiment.

In another alternative design of the axial and axial/tail slap testing machines of FIGS. 1-5, another variation of the first embodiment of shock testing machine is shown in FIG. 6, referred to generally with reference number 210. In FIG. 6, the breaks on the left and right of the machine are used to denote a long length of the components being broken. Furthermore, the guide rails 216 are not shown extended past the test platform 212 for simplicity. In the shock testing machine 210, similar to the shock testing machine 200 of FIG. 5, the test platform 212 and the braking unit 214 are still movable over separate pairs of overlaying rails 216, 218. However, the braking pads of the test platform 212 are initially engaged inside the brake engagement pathway gap of the braking unit 214. In a simple version of this design, the engaging test platform 212 and braking unit 214 are initially stationary. An impact mass 220, which rides over the braking unit rail 218, is accelerated towards the braking unit by the aforementioned bungee cords 102. The impact mass 220 will then impact the braking unit 214, forcing it to begin to travel towards the left as seen in FIG. 6 with a resulting initial velocity which is dependent on the mass of the impact mass 220 and the braking unit 214. The braking unit 214, through the test platform braking pads, will then exert a nearly constant force to the test platform 212 until their relative velocity vanishes. The nearly constant braking force results in a near constant acceleration of the test platform 212 with very sharp rise and fall times, i.e., resulting in a near square wave acceleration profile. This design can also be provided with the earlier described tail-slap mechanism of FIG. 4.

A second embodiment of shock and shock/tail-slap testing machines are intended to apply high peak and short duration acceleration and deceleration pulses, such as over ±10,000 g over long durations, such as well over 5 msec. These shock loading machines can apply one or a combination of shock loading pulses to the test object, such as to an ordnance in the axial and lateral directions to simulate almost any shock loading events, including tail-slaps, where large lateral accelerations/decelerations are introduced due to the bending and rebound of the ordnance in the lateral direction.

Figure 7:
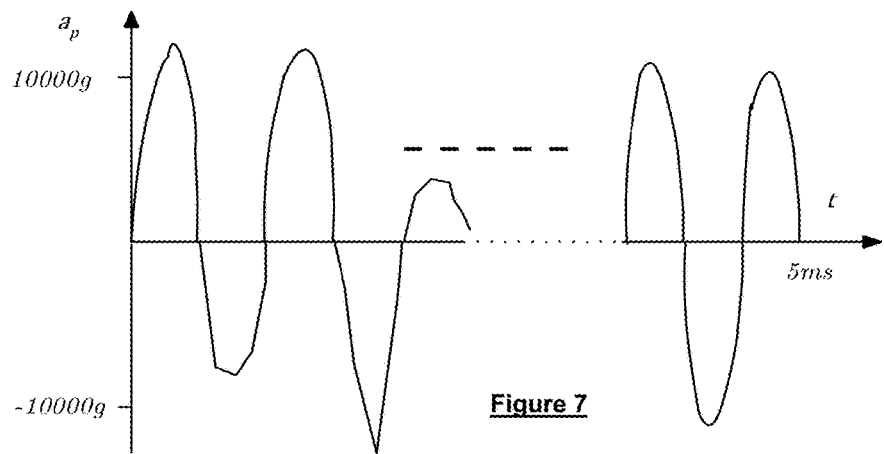
FIG. 7 illustrates an acceleration vs. time plot for short duration acceleration and deceleration pulses over relatively long durations.

Such embodiment of shock and shock/tail-slap testing machines can apply sequences of short duration acceleration and deceleration pulses, such as with peaks of around ±10,000 g over relatively long durations, such as over 5 msec, shown in the acceleration vs. time plot of FIG. 7. A simple calculation will the show that to achieve a peak acceleration of $a_p=\pm 10,000$ g, for a range of test article mass m of 10 lbs. to 250 lbs. (assuming zero mass for the test platform and its other required moving parts), the required peak force $F_p$ is as given in the Table 1 below.

TABLE 1

Peak force to achieve ±10,000 g acceleration/deceleration.

| | Test Article Weight (lbs.) | | |
|---|---|---|---|
| | 10 | 100 | 250 |
| Peak force (lbf) | 97,800 | 978,000 | 2,445,500 |

As can be seen, the required peak force levels are seen to be large but very short in duration, indicating that the best method of providing the desired short duration and high peak acceleration/deceleration shock loading is by impact loading. It is noted that a common method of applying acceleration/deceleration cycles to a test article when the peak acceleration levels and the mass of the test article are relatively low is by constructing a mass-spring type of vibrating system and exciting the system in resonance. However, to use a vibrating system to achieve ±10,000 g peak acceleration/deceleration levels would require a very stiff spring (structurally flexible) structure, even for the test articles of 10 lbs. in weight, which for a vibration cycle period of even around 0.1 msec, means that the vibrating system has to vibrate at 10,000 Hz. Such a vibratory system for direct excitation at resonance is obviously impractical.

Thus, a system that could provide short duration (of the order of 0.1 msec cycle period) and high peak acceleration/deceleration (of the order of ±10,000 g) shock loading is based herein on high frequency impact type loading.

In addition, as is shown below, the very high impact peak and low duration acceleration/deceleration pulses can be generated at relatively slow velocities of an impacting mass if the impact is with a massive, grounded (fixed), high strength and dense mass (barrier), and if the impacting surfaces are properly shaped to minimize elastic deformation and eliminate local plastic deformation.

Figure 8:
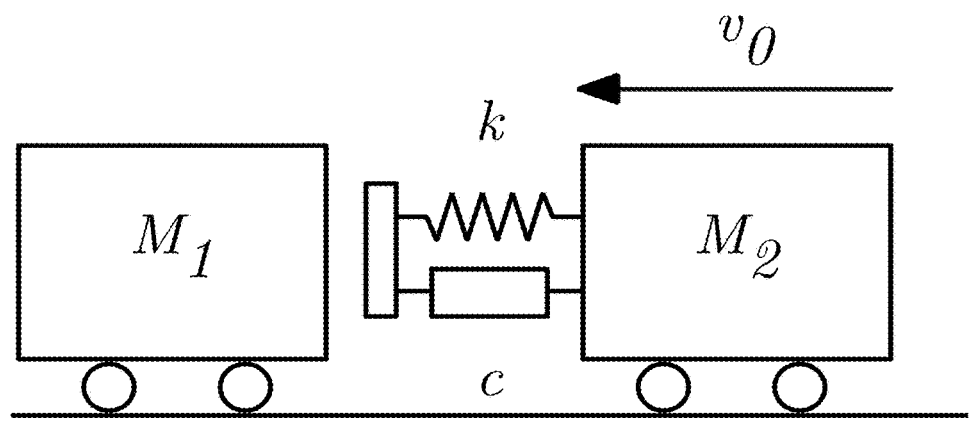
FIG. 8 illustrates a schematic model of two masses impacting each other.

Consider the two relatively rigid objects $M_1$, $M_2$ shown in FIG. 8. Consider the case in which the mass $M_2$ traveling at the velocity $v_0$ impacts the larger stationary $M_1$ (to which the test article is rigidly attached and its mass having been included in the indicated mass $M_1$). The spring rate k and damper c are considered to represent the linear approximation of the local deformation during the process of impact between the two objects $M_1$ and $M_2$. The values of the spring and damping rates k and c are dependent on the material characteristics and overall mass and geometry and structural construction of the two objects, and the geometry of their impacting surfaces. In this simple model, the damping element c is considered to provide the means to account for a generally nonlinear process of mechanical energy loss during impact, which for relatively stiff steel structures has been indicated as resulting in a coefficient of restitution of around 0.5-0.8.

Using a simple dynamic impact model with the coefficient of restitution of 0.7, the initial velocity $v_0$ that the mass $M_2$ requires to impart an acceleration pulse with a peak of 10,000 g on the mass $M_1$ for a desired duration can then be estimated. For example, for a given mass $M_1$=15 lbs., to generate an impact acceleration with a peak of $a_p$=10,000 g and impact pulse durations of 0.05 and 0.1 msec, two possible combinations of mass $M_2$ and its initial velocity $v_0$ are provided in the Table 2 below. It is noted that since impact duration is dependent on the material characteristics and geometry of the impacting objects and the contact surface geometries, the possible impact durations of 0.05 and 0.1 msec, which were obtained using Finite Element software for typical solid objects made out of steel, are being used in Table 2 below.

TABLE 2

| | Impact Duration t (msec) | |
|---|---|---|
| | 0.05 | 0.1 |
| $M_2$ (lbs) | 1 | 2 |
| $v_0$ (m/s) | 33 | 35 |

If the mass $M_1$ is considered to be 150 lbs. or 375 lbs., to generate a similar acceleration pulse profile with a peak of $a_p$=10,000 g with the indicated impact pulse durations, a number of possible combinations of mass $M_2$ and its initial velocity $v_0$ are provided in the Tables 3 and 4 below. It is noted that the above $M_2$ mass levels of 15 lbs., 150 lbs. and 375 lbs. are considered to represent the mass of the object being tested plus the mass of the testing platform on which the test object is mounted.

TABLE 3

| | Impact Duration t (msec) | | | | | |
|---|---|---|---|---|---|---|
| | 0.05 | | 0.1 | | 0.2 | |
| $M_2$ (lbs) | 1 | 10 | 2 | 20 | 4 | 40 |
| $v_0$ (m/s) | 311 | 33 | 313 | 35 | 317 | 39 |

As can be seen in Tables 2-4, and considering that a mass $M_2$ speed of around 35-60 m/s (equivalent to 126-216 Km/hr) or slightly higher is achievable, particularly for smaller mass $M_2$, in general for longer durations impacts and larger impacting masses $M_2$ the desired $a_p$=10,000 g should be possible to achieve. However, since impacting mass $M_2$ speeds of around 300 m/s (or around 1,100 Km/hr) requires gun firing of projectiles, in which case the impact coefficient of restitution, even by proper selection of materials and geometries for both mass elements, will be closer to 1, thereby requiring multiple such shots around 1 msec apart, which is not an easy task to achieve. In addition, the testing process will no longer be relatively low cost and the testing system can no longer be considered to be reusable.

TABLE 4

| | Impact Duration t (ms) | | | |
|---|---|---|---|---|
| | 0.2 | | 0.3 | |
| $M_2$ (lbs) | 8 | 80 | 16 | 160 |
| $v_0$ (m/s) | 394 | 47 | 302 | 41 |

In the above example, one may also consider both mass $M_1$ and mass $M_2$ to be moving with certain velocity towards each other, thereby making it possible to achieve higher relative impact velocities and thereby higher peak impact accelerations.

As can be seem from the above examples, impact between relatively stiff bodies can generate short duration and high peak acceleration pulses to test objects mounted on the impacted object. Such types of shock testing machines in which one or more mass elements are used to impact the test platform at high speeds in one or multiple directions, however have the following, mostly practical, shortcomings:

1. It is very difficult, if not impossible, to achieve multiple impacts spaced at very short times apart (of the order of 1 msec);
2. Since each impact also causes the test platform to be displaced, it makes it very difficult to provide multi-axial impacts that are spaced very short times apart;
3. As can be seen in Tables 2-4, to achieve the desired high peak acceleration levels, one would need to either use a relatively large impact mass or smaller mass with very high impact speed.

Figure 9:
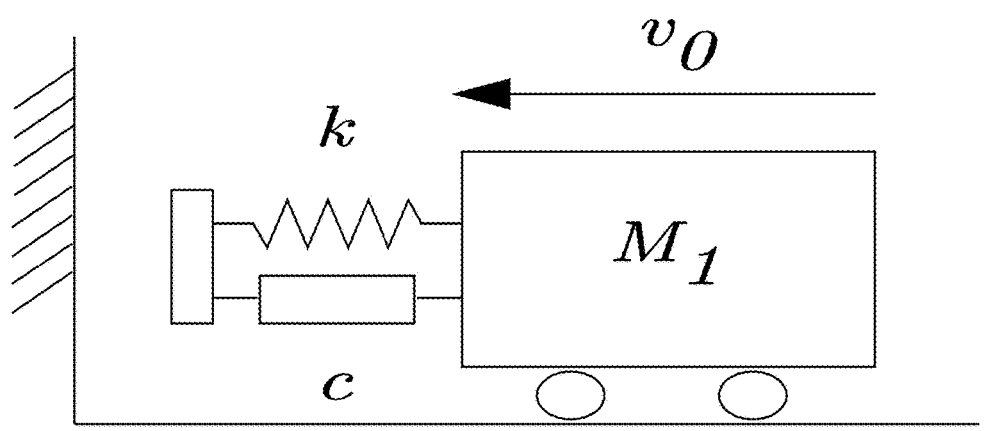
FIG. 9 illustrates a schematic model of a mass impacting a rigid fixed barrier.

Consider the case in which a rigid mass $M_1$ moving at a velocity $v_0$ impact a rigid fixed barrier (wall) as shown in FIG. 9. In FIG. 9, the spring rate k and damper c are considered to similarly represent the linear approximation of the local deformation during the process of impact between the mass $M_1$ and the fixed barrier. In this simple model, the damping element c is considered to provide the means to account for generally nonlinear process of mechanical energy loss during impact, which for relatively stiff steel structures has been shown to result in a coefficient of restitution of around 0.5-0.8.

As an example, consider a steel cube of 0.2 m per side weighing 62 Kg (140 lbs) impacting a relatively large grounded steel slab on one side at a velocity of 5 m/sec. If the impact coefficient is considered to be 0.7, a finite element model and analysis of the impact cycle (done using finite element software) indicates an impact duration of about 0.12 msec and by fitting the resulting deceleration/acceleration curve profile with a half sine curve, a peak deceleration of $a_p$=10,222 g is found to be generated.

A second embodiment of shock testing machine provides multi-axial short duration acceleration/deceleration pulses with very high peaks to relatively heavy objects (here by object it is meant the test object as mounted on a test platform). Such a machine generates the short duration and high peak acceleration/deceleration pulses by the impact of the test platform (to which the test object is attached) with a large and rigid grounded mass, thereby as was shown above, can achieve the highest possible short duration impact generated acceleration/deceleration peaks. Such a machine allows multi-axis impact generated pulses that are sub-milliseconds apart for very long time durations (such as well over 10-20 msec). The total motion of the impacting mass (test platform with attached test object) in each multi-axial impact direction is very small (e.g., a total of 4 mm in the example below with a total test platform and test object mass of 150 lbs.). As a result, all sensor data collection and powering wire harnesses can be used to directly connect onboard instrumentations to the data collection instrumentation equipment being used. As a result, there is no limitation on the amount of data that can be collected during each testing and onboard recording devices are not required. As discussed below, such a machine is provided with flywheels that function as sources of a large amount of mechanical energy that would allow it to sustain short duration and high peak acceleration/deceleration pulses over relatively long periods of time.

Figure 10:
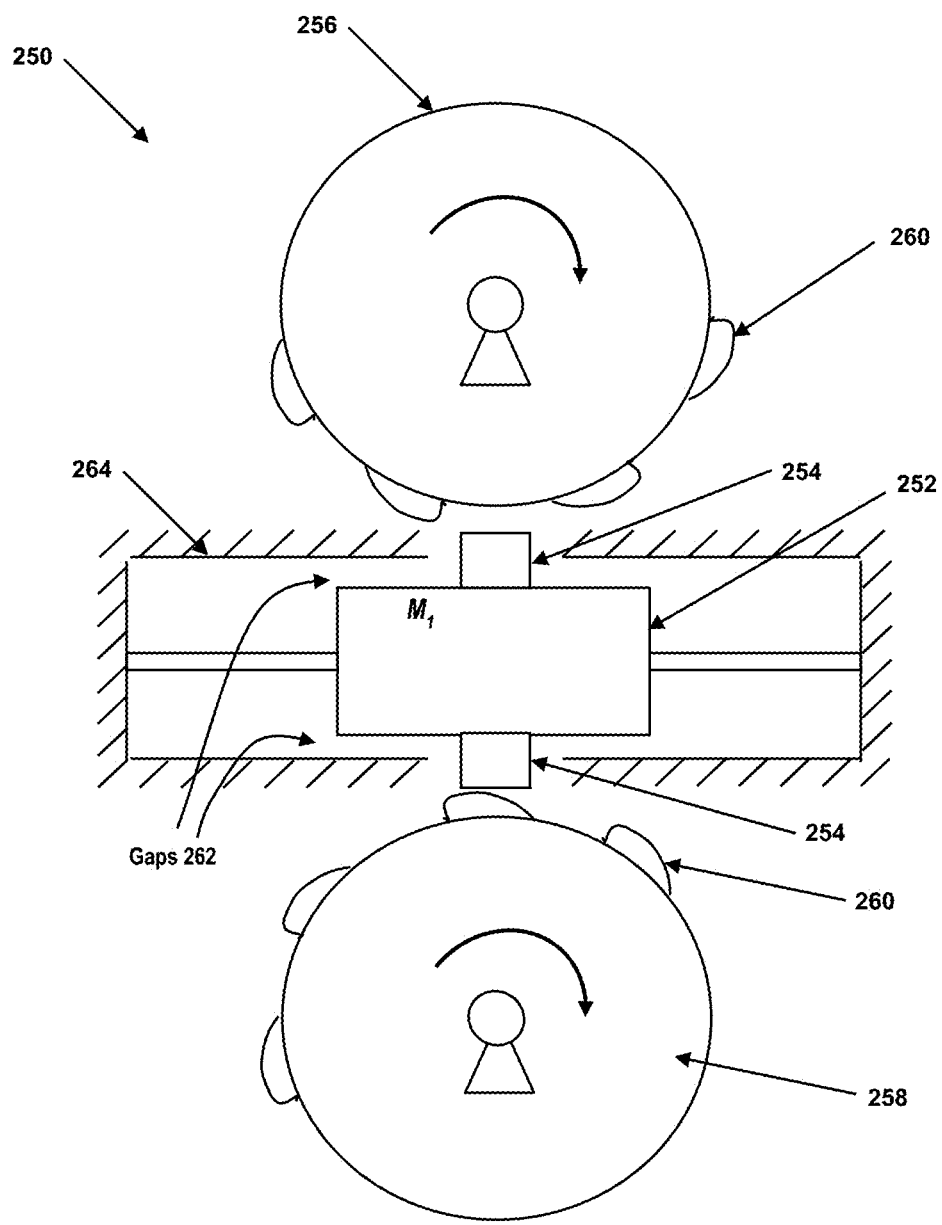
FIG. 10 illustrates a perspective view of a second embodiment of a shock testing machine.

A second embodiment of shock testing machine for multi-axial short duration and high peak acceleration/deceleration shock/tail-slap loading is shown in FIG. 10 and generally referred to by reference numeral 250. In this illustration and for the sake of simplicity, a single axis version of the machine is shown with a multi-axial design discussed below. The test platform 252 and test object attached thereto (not shown) are considered to have a mass $M_1$. The mass $M_1$ is attached to the grounded machine structure via a relatively flexible structure (beams, not shown in FIG. 10, can be replaced by a centrally and relatively flexible column 256 in the alternative version of FIG. 11 to allow the mass $M_1$ to impact in two perpendicular directions by a second set of flywheels and impact stops). The main function of the flexible structure in this machine is to ensure that the mass $M_1$ stays in its illustrated plane of motion and is not provided for the purpose of a centering/returning force, i.e., in fact it functions as a zero friction planar bearing rather than a spring element.

Two flywheels 256, 258 with equally spaced cams 260 are provided which would engage side engagement surfaces 254 on each side of the mass $M_1$ element. Although only four cams 260 are shown on the flywheels 256, 258 are shown in FIG. 10, the same is only shown for simplicity and the cams 260 are equally spaced about the entire circumference of the flywheels 256, 258. The cams 260 on each flywheel 256, 258 are synchronized to alternatively displace the mass $M_1$ towards the other flywheel by appropriate motors and controls (not shown). Very small gaps 262 are provided between the mass $M_1$ and the stops 264 (shown as ground in FIG. 10) of the relatively massive and grounded structure of the machine. The rotational speed of the flywheels 256, 258, the cam 260 profiles and their positioning relative to the side engagement surfaces of the mass $M_1$ are designed to accelerate the mass $M_1$ away from the engaging flywheel to a prescribed impact speed. The mass $M_1$ will then impact stops 264 provided on the surfaces of the machine structure, thereby imparting a very short duration but high peak acceleration/deceleration pulse to the mass $M_1$. Following each impact, the flywheel cam adds energy to the mass $M_1$ by accelerating it in its direction of travel following an impact to bring it close to the aforementioned prescribed impact velocity for its impact to the stops provided on the opposite side of the machine structure. As a result, almost as many of the short duration and high acceleration/deceleration impact pulses as desired may be produced with the flywheels supplying mechanical energy to the mass $M_1$ to compensate for the mechanical energy that is lost during each impact event. It is noted that the machine would still operate successfully even if the impact of the mass $M_1$ is not fully synchronized with the motion of the flywheels and that the flywheel cams do not engage the mass $M_1$ just after an impact as will be described below by studying different impact and flywheel positioning scenarios.

By way of example, the test platform 252 and test object attached thereto total mass can be $M_1$=150 lbs (68 Kg) and the gaps 262 between the mass 252 and the impacting stops 264 can be 2 mm. With a predicted coefficient of restitution of 0.6, the required mass $M_1$ velocity for impacting the stops on the massive grounded structure of the machine to achieve a peak acceleration/deceleration pulse of 10,000 g is about 5 m/sec and the impact pulse duration is found from finite element software simulation to be about 0.08 msec. The return velocity of the mass $M_1$ after each impact is calculated to be around 3 m/sec. The engaging flywheel cam 260 is therefore required to accelerate the mass $M_1$ from 3 m/sec to 5 m/sec during its around 4 mm travel back to the opposite machine structure stops 264. The process is then repeated by the engagement of a cam 260 from the opposite flywheel 256, 258. The process may be continued for almost any desired duration.

In the above example, the generated 0.08 msec acceleration/deceleration pulses with 10,000 g peak occur every 1 msec and may be generated by a 20 inch diameter flywheel rotating at around 1,500 rpm with each cam spanning around 10 degrees of the flywheel periphery with a similar spanning gaps between the cams. In the partial view of FIG. 11

Figure 11:
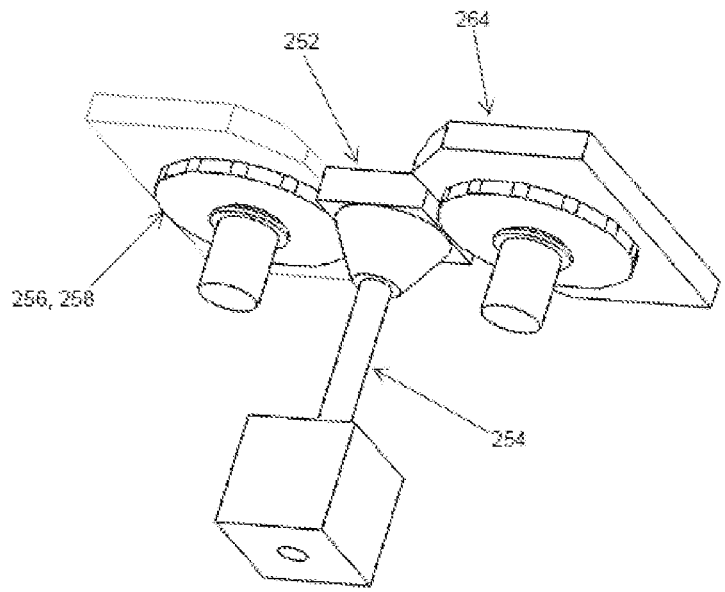
FIG. 11 illustrates a perspective view of a variation of the second embodiment shock testing machine of FIG. 10 having a central flexible element and only showing one of the flywheels.

(shown without one of the flywheels and without a machine base or flywheel motor), the mass $M_1$ is shown to be mounted on a relatively flexible column 254 that minimally resists its planar bending (e.g., +/−2 mm) in any direction. In FIG. 11, to clearly show the basic components of the machine, only one flywheel 256 for generating the indicated impact pulses is shown. In the actual design, a similar flywheel 258 is provided to generate similar short duration and high peak impact acceleration/deceleration pulses in an opposite perpendicular direction, to provide the means of achieving multi-axial short duration and high peak impact acceleration/deceleration pulses.

Figure 12:
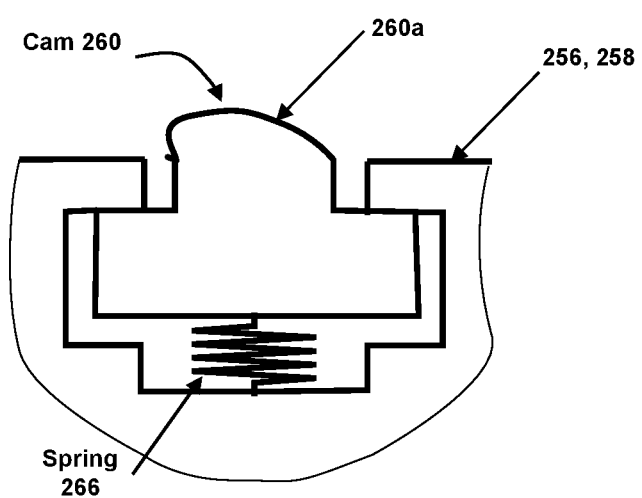
FIG. 12 illustrates an alternative cam configuration for the flywheels of the second embodiment shock testing machine of FIG. 10.

In the example provided above, it is noted that the flywheel cams are intended to accelerate the mass $M_1$ from its post impact velocity of 3 m/sec to a velocity of 5 m/sec for its next 10,000 g impact. The cam actuated acceleration can begin right after each impact in the indicated distance of 4 mm and during 1 msec. Under these circumstances, the cam is readily calculated to require to accelerate the mass $M_1$ at a rate of around 200 g, which indicates that the cam must apply a force of around 136,000 N (31,000 lbs) to the mass $M_1$. Considering the worst possible impact and cam positioning in which a cam is in the maximum extension towards the mass $M_1$ at which the mass has just impacted the stops on the opposite wall, then the mass $M_1$ would impact the cam surface with a velocity of 3 m/sec, which would generate an impact peak force of significantly greater than the above 31,000 lbs. However, such high impact shock loading events between the mass $M_1$ and the flywheel cams can be averted by limiting the compressive loading that the mass $M_1$ can apply to a cam 260. This may, for example, be accomplished as shown in FIG. 12 by providing preloaded compressive springs 266 to limit the force that can be applied to the cam 260 by the mass $M_1$. The springs 266 (such as Bellville washers) can be preloaded (e.g., in the example provided above, to around the aforementioned 31,000 lbs) and would begin to deform, i.e., retract the cam surface 260a away from the mass $M_1$ as the contact force level tends to go beyond the preloading force. In the example provided above, the maximum retracting distance that must be provided for the cam 260 is 4 mm, along which the preloaded springs can be designed to exhibit minimal force increase.

It is also noted that the impact force limiting cam design shown in FIG. 12 can also provide the means of starting the multi-axial short duration and high peak impact shock/tail slap loading by limiting initial impact load levels between the cams 260 and the mass $M_1$. Several options also exist for rapid initiation of the multi-axial impact induced shock loadings. For example, pairs of flywheels may be geared together and via a clutching system engage to a third larger flywheel for rapid acceleration to the required rpm. Other options include the use of hydraulic pistons to rapidly move the system flywheels the required 4 mm forward towards the mass $M_1$. Alternatively, the base of the preloaded spring elements of the cams may be retracted back to allow the cams to move back 4 mm, thereby not engage the mass $M_1$, and then be rapidly pushed forward to engage the cams with the contacting surfaces of the mass $M_1$.

Furthermore, although the shock testing machine 250 of FIG. 10 utilizes a pair of flywheels, those skilled in the art will appreciate that a single flywheel may also be utilized.

Although the novel shock testing machines and methods as covered herein is born from the specific needs of munitions, a technology that can reliably provide a very smooth shock, which is highly repeatable and lasts a relatively long amount of time has numerous commercial applications, particularly at a relatively inexpensive cost, including aircraft and satellite components, consumer electronic components, such as circuit boards and device casings, and automobile, light and heavy truck components.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A shock testing machine comprising:
   a test platform upon which one or more objects to be tested are mounted;
   one or more rails upon which the test platform is movable; and
   a braking station having one or more braking elements operatively engageable with one or more corresponding braking surfaces on the test platform after the test platform has moved a predetermined distance relative to the braking station, wherein the one or more braking elements are movable to vary a gap between the one or more braking elements and the one or more braking surface; and
   the one or more braking elements comprise a beveled region such that a portion of the braking element in the beveled region has a thickness that increases with a direction of travel of the test platform.

2. The shock testing machine of claim 1, further comprising one or more actuators for moving the braking elements.

3. The shock testing machine of claim 2, wherein the one or more actuators comprise one or more piezoelectric actuators.

4. A method for shock testing one or more objects, the method comprising:
   mounting the one or more objects to a test platform;
   movably disposing the test platform on one or more rails;
   moving the test platform a predetermined distance relative to a braking station;
   varying a braking amount of the braking station by varying a gap between one or more braking elements at the braking station and one or more corresponding braking surfaces at the test platform; and
   braking the test platform by contacting the one or more braking elements with the corresponding one or more braking surfaces.

* * * * *